United States Patent [19]
Nihira et al.

[11] Patent Number: 6,111,059
[45] Date of Patent: Aug. 29, 2000

[54] DIAMINOBENZENE DERIVATIVES, POLYIMIDES PREPARED THEREFROM, AND ALIGNMENT FILM FOR LIQUID CRYSTALS

[75] Inventors: Takayasu Nihira; Hideyuki Nawata; Hiroyoshi Fukuro, all of Funabashi, Japan

[73] Assignee: Nissan Chemical Industries, Ltd., Tokyo, Japan

[21] Appl. No.: 09/125,043

[22] PCT Filed: Feb. 12, 1997

[86] PCT No.: PCT/JP97/00358

§ 371 Date: Aug. 12, 1998

§ 102(e) Date: Aug. 12, 1998

[87] PCT Pub. No.: WO97/30107

PCT Pub. Date: Aug. 21, 1997

[30] Foreign Application Priority Data

Feb. 15, 1996 [JP] Japan ................................ 8-028020

[51] Int. Cl.$^7$ .................................................. C08G 73/10
[52] U.S. Cl. ............................ 528/353; 528/125; 528/128; 528/171; 528/172; 528/173; 528/179; 528/183; 528/185; 528/188; 528/220; 528/229; 528/350; 562/147; 428/1; 428/473.5
[58] Field of Search ........................ 562/147; 428/473.5; 528/125, 128, 171–173, 179, 183, 185, 188, 220, 229, 350, 353

[56] References Cited

U.S. PATENT DOCUMENTS 5,608,033 3/1997 Nihira et al. .......................... 528/353
5,665,856 9/1997 Nihira et al. .......................... 528/353

FOREIGN PATENT DOCUMENTS 3-121132 5/1991 Japan .
3-179323 8/1991 Japan .
8-12759 1/1996 Japan .

*Primary Examiner*—P. Hampton-Hightower
*Attorney, Agent, or Firm*—Oblon, Spivak, McClelland, Maier & Neustadt, P.C.

[57] ABSTRACT

A diaminobenzene derivative represented by formula (1), and a polyimide obtained by reacting a diamine containing at least 1 mol % of said diaminobenzene derivative, with a tetracarboxylic acid and its derivatives to obtain a polyimide precursor and ring-closing it, having a repeating unit represented by formula (2), and a liquid crystal alignment film containing said polyimide.

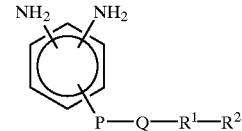

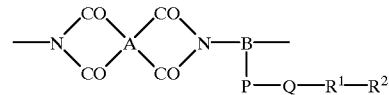

P is a single bond or —O—, —COO—, or —CONH—, Q is a cyclic substituent selected from an aromatic ring, an aliphatic ring, a hetero ring and their substitution products, $R^1$ is an aliphatic ring, and $R^2$ is $C_{1-22}$ straight chain alkyl group, A is a tetravalent organic group constituting a tetracarboxylic acid, B is a bivalent organic group constituting a diamine.

20 Claims, No Drawings

DIAMINOBENZENE DERIVATIVES, POLYIMIDES PREPARED THEREFROM, AND ALIGNMENT FILM FOR LIQUID CRYSTALS

TECHNICAL FIELD

The present invention relates to a novel diaminobenzene derivative, a polyimide synthesized by using the compound as one of stating materials, and a liquid crystal alignment film employing the polyimide. More particularly, it relates to a diamine having a specific structure, which is industrially readily producible, a polyimide employing it, and a liquid crystal alignment film employing the polyimide. The polyimide synthesized by using the diamine of the present invention, is particularly useful for an alignment film of a liquid crystal display device.

BACKGROUND ART

Heretofore, polyimides have been widely used as protecting materials or insulating materials in the electric and electronic fields, by virtue of high mechanical strength, heat resistance and solvent resistance, as their characteristics. However, developments in the electric and electronic fields in recent years have been remarkable, and increasingly high properties have been required also for materials to be used. Especially in the application to alignment films for liquid crystal display devices, polyimides have been mainly employed because of the uniformity and durability of the coating film surface. However, in an attempt for high densification and high performance of liquid crystal displays, the surface properties of polyimide coating films have become important, and it has become necessary to impart a new property which conventional polyimides do not have.

A liquid crystal display device is a display device utilizing an electro-optical change of liquid crystal and has undergone a remarkable development as a display device for various displays in recent years in view of the characteristics such that it is small in size and light in weight as a device and its power consumption is small. Especially, a twisted nematic type (TN-type) electric field effect liquid crystal display device is a typical example, wherein nematic liquid crystal having positive dielectric anisotropy is employed so that liquid crystal molecules are aligned in parallel with a substrate at the interface of each of a pair of mutually opposing electrode substrates, and the two substrates are combined so that the directions for alignment of liquid crystal molecules are orthogonal to each other.

In such a TN-type liquid crystal display device, it is important that long axis directions of liquid crystal molecules are aligned uniformly in parallel with the substrate surface and further that the liquid crystal molecules are aligned with a certain inclined alignment angle (hereinafter referred to as a tilt angle) against the substrate. As typical methods for aligning liquid crystal molecules in such a manner, two methods have been known heretofore.
The first method is a method which comprises vapor depositing an inorganic substance such as silicon oxide from an oblique direction to a substrate to form an inorganic film on the substrate, so that the liquid crystal molecules are aligned in the direction of vapor deposition. This method is not industrially efficient, although uniform alignment with a constant tilt angle can be obtained.
The second method is a method which comprises forming an organic coating film on a substrate surface, and rubbing its surface in a predetermined direction with a cloth of e.g. cotton, nylon or polyester, so that liquid crystal molecules are aligned in the rubbing direction. By this method, constant alignment can be obtained relatively easily, and industrially, this method is primarily employed. As the organic film, polyvinyl alcohol, polyoxyethylene, polyamide or polyimide may, for example, be mentioned. However, from the viewpoint of the chemical stability, thermal stability, etc., polyimide is most commonly employed.

In the field of liquid crystal alignment films, it has been difficult to obtain a high tilt angle constantly by the method of rubbing an organic film such as polyimide. As a means to solve such difficulty, JP-A-62-297819 proposes a treating agent for liquid crystal alignment made of a mixture of a long chain alkyl compound with a polyimide precursor. Further, JP-A-64-25126 discloses a treating agent for liquid crystal alignment made of a polyimide using, as a starting material, a diamine having an alkyl group. Thus, many attempts have been made to increase the tilt angle of liquid crystal by introducing an alkyl group into polyimide, and it has been made possible to increase the tilt angle.

However, with the above mentioned liquid crystal alignment film having an alkyl group introduced into polyimide, the thermal stability of the tilt angle was inadequate. Namely, conventional polyimide alignment films having an alkyl group introduced, had a problem that the tilt angle tended to decrease when heated at a temperature of at least the isotropic temperature of liquid crystal (hereinafter referred to as isotropic treatment), although the tilt angle immediately after injection of liquid crystal can be increased. Especially when the tilt angle is high, or the curing temperature during formation of the alignment film is low, the decrease in the tilt angle by the isotropic treatment becomes remarkable. Further, when a polyimide film is formed on a substrate, it is common to have the film baked at a high temperature of from 200 to 300° C., and there was a problem that since the heat resistance of the alkyl side chain itself was not sufficient, the tilt angle tended to decrease or non-uniformity tended to result especially in high temperature baking. These problems are extremely important questions to be solved to accomplish a uniform liquid crystal display with a higher contrast in the future liquid crystal display device, and a polyimide alignment film has been very much desired which not only has a high tilt angle but also presents a thermally more stable tilt angle.

DISCLOSURE OF THE INVENTION

The present invention has been accomplished as a result of a detailed and systematic study to improve the thermal stability of the tilt angle of liquid crystal by a liquid crystal alignment film.

Namely, the present invention relates to a diaminobenzene derivative represented by the general formula (1):

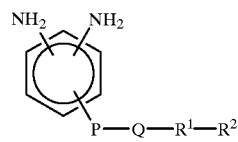

[1]

(wherein P is a single bond or a bivalent organic group selected from —O—, —COO— and —CONH—, Q is a cyclic substituent selected from an aromatic ring, an aliphatic ring, a hetero ring and their substitution products, $R^1$ is an aliphatic ring, and $R^2$ is a $C_{1-22}$ straight chain alkyl group is 1.

Further, the present invention relates to polyimide obtained by reacting a diamine containing at least 1 mol % of the diaminobenzene derivative represented by the above general formula (1), with a tetracarboxylic acid and its derivative to obtain a polyimide precursor having a viscosity of from 0.05 to 5.0 dl/g (in N-methylpyrrolidone at a temperature of 30° C., concentration: 0.5 g/dl) and ring-closing it, and having a repeating unit represented by the general formula (2):

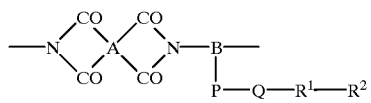

[2]

(wherein A is a tetravalent organic group constituting a tetracarboxylic acid, B is a bivalent organic group constituting a diamine, and P, Q, $R^1$ and $R^2$ are the same as in the above Formula (1)).

Further, the present invention relates to a liquid crystal alignment film comprising a polyimide containing at least 1 mol % of the repeating unit represented by the above formula (2).

Now, the present invention will be described in detail.

BEST MODE FOR CARRYING OUT THE INVENTION

The diaminobenzene derivative of the present invention is easy to synthesize and is useful as a starting material for e.g. polyimide or polyamide. Further, this is used as one of materials to obtain a polyimide having a certain specific cyclic substituent on a side chain. This polyimide is useful particularly for an application to an alignment film for a liquid crystal display device, whereby alignment of liquid crystal is excellent, and it is possible to obtain a thermally stable high tilt angle.

Particularly, it is one of important objects of the present invention to increase the tilt angle of liquid crystal and to improve its thermal stability, by using, as a liquid crystal alignment film, a polyimide having a certain specific cyclic substituent, obtainable from the diaminobenzene derivative. For this purpose, Q in the general formula (1) is a cyclic substituent such as an aliphatic cyclic substituent, an aromatic cyclic substituent or a heterocyclic substituent in order to increase the thermal stability of the cyclic side chain, and the aliphatic cyclic substituent for Rl is essential for the improvement of the thermal stability of the tilt angle, and $R^2$ being a $C_{1-22}$ straight chain alkyl group, is essential to control the degree of the tilt angle. These substituents are connected to the polyimide main chain via the connecting portion P.

The diaminobenzene derivative represented by the general formula (1):

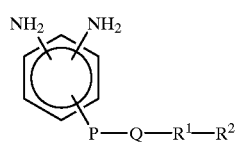

[1]

is a diamine having a specific structure and is constituted by the diamine portion

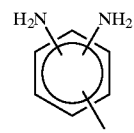

the connecting portion P, the cyclic substituents Q and $R^1$ and the linear alkyl group portion $R^2$. Its synthetic method is not particularly limited. For example, it can be synthesized by the following method.

In a synthesis of a diamine, it is common to synthesize the corresponding dinitro compound represented by the general Formula (II):

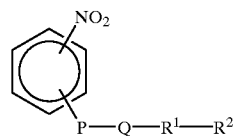

[11]

and to reduce the nitro groups by a usual method to convert them into amino groups.

The connecting portion P is a connecting group such as a single bond (linkage only), an ether bond —O—, an ester bond —COO— or an amide bond —CONH—, and such a connecting group can be formed by a usual organic synthetic method. For example, in the case of an ether bond, it is common to react the corresponding halogen derivative and hydroxyl group-substituted derivative in the presence of an alkali, and in the case of an amide bond, it is common to react the corresponding acid chloride and amino group-substituted derivative in the presence of an alkali.

As a specific example of the material for forming the dinitro moiety, a dinitrobenzene substituted by a substituent for forming the connecting portion P, such as a halogen atom, a hydroxyl group or a halogenated acyl group, may be mentioned. Specific examples of such a substituted dinitrobenzene include 2,3-dinitrobenzene, 2,4-dinitrobenzene, 2,5-dinitrobenzene, 2,6-dinitrobenzene, 3,4-dinitrobenzene and, 3,5-dinitrobenzene. From the viewpoint of the availability of the material and the reactivity during the polymerization of polyimide, it is most common to employ 2,4-dinitrochlorobenzene, 2,4-dinitrophenol or 2,4-dinitrobenzoic acid chloride.

Specific examples of the cyclic substituent Q in the general Formula (1) may be cyclic substituents including aliphatic cyclic substituents such as a cyclohexane ring, a bicyclohexyl ring and a tercyclohexyl ring, aromatic rings such as a benzene ring, a biphenyl ring and a terphenyl ring, and hetero rings such as a phenylpyrimidine ring.

For the cyclic substituent Q of the present invention, these cyclic compounds and their analogues may be employed. From the viewpoint of the availability of the materials and easiness of the synthetic reaction, it is preferred to employ, as Q, a cyclohexane ring, a benzene ring or a biphenyl ring. Particularly preferred is a benzene ring.

As specific examples of the aliphatic cyclic substituent $R^1$ in the general Formula (1), aliphatic cyclic substituents such as cyclohexane, a bicyclohexyl ring and a tercyclohexyl ring, may be mentioned. For the aliphatic cyclic substituent $R^1$ of the present invention, these cyclic compounds and their analogues may be employed. However, from the viewpoint of the availability of the starting materials and easiness of the synthetic reaction, it is preferred to employ, as $R^1$, a cyclohexane ring or a bicyclohexyl ring.

$R^2$ in the general Formula (1) is a $C_{1-22}$, preferably $C_{3-10}$, straight chain alkyl group. The carbon number may suitably be selected in order to obtain the desired tilt angle, when the corresponding polyimide is used as an alignment film.

Various methods are available as the method for connecting Q, $R^1$ and $R^2$. However, it is possible to suitably connect them by means of a common organic synthetic method, such as Grignard reaction, a Friedel-Crafts acylation method for an aromatic ring or a Kishner reduction method.

The diaminobenzene derivative of the present invention represented by the above general formula (1) obtainable by the above-mentioned preparation method, may be subjected to polycondensation with a tetracarboxylic acid and its derivative, such as a tetracarboxylic acid, a tetracarboxylic acid dihalide or a tetracarboxylic dianhydride to synthesize a polyimide having a specific structure at its side chain.

The method for obtaining the polyimide of the present invention, is not particularly limited. Specifically, it can be obtained by reacting and polymerizing the above diamine with a tetracarboxylic acid and its derivative to obtain a polyimide precursor, followed by ring-closing imide conversion.

The tetracarboxylic acid and its derivative to be used to obtain the polyimide of the present invention, is not particularly limited.

Specific examples thereof include aromatic tetracarboxylic acids such as pyromellitic acid, 2,3,6,7-naphthalene tetracarboxylic acid, 1,2,5,6-naphthalene tetracarboxylic acid, 2,3,6,7-anthracene tetracarboxylic acid, 1,2,5,6-anthracene tetracarboxylic acid, 3,3', 4,4'-biphenyl tetracarboxylic acid, 2,3,3', 4-biphenyl tetracarboxylic acid, bis(3,4-dicarboxyphenyl)ether, 3,3', 4,4'-benzophenone tetracarboxylic acid, bis(3,4-dicarboxyphenyl)sulfone, bis(3,4-dicarboxyphenyl)methane, 2,2-bis(3,4-dicarboxyphenyl) propane, 1,1,1,3,3,3-hexafloro-2,2-bis(3,4-dicarboxyphenyl)propane, bis(3,4-dicarboxyphenyl) dimethyl silane, bis(3,4-dicarboxyphenyl)diphenyl silane, 2,3,4,5-pyridine tetracarboxylic acid, and 2,6-bis(3,4-dicarboxyphenyl)pyridine, and their dianhydrides and their dicarboxylic acid diacid halides; alicyclic tetracarboxylic acids such as 1,2,3,4-cyclobutane tetracarboxylic acid, 1,2,3,4-cyclopentane tetracarboxylic acid, 1,2,4,5-cyclohexane tetracarboxylic acid, 2,3,5-tricarboxycyclopentyl acetic acid, and 3,4-dicarboxy-1,2,3,4-tetrahydro-1-naphthalene succinic acid, and their dianhydrides and their dicarboxylic acid diacid halides; and aliphatic tetracarboxylic acids such as 1,2,3,4-buthane tetracarboxylic acid, and their dianhydrides and their dicarboxylic acid diacid halides.

Especially for application to alignment films, alicyclic tetracarboxylic acids and their dianhydrides and their dicarboxylic acid diacid halides are preferred from the viewpoint of the transparency of the coating film. Particularly preferred are 1,2,3,4-cyclobutane tetracarboxylic dianhydride and 3,4-dicarboxy-1,2,3,4-tetrahydro-1-naphthalene succinic dianhydride. Further, one or more of these tetracarboxylic acids and their derivatives may be used in admixture.

In the present invention, the tetracarboxylic acid and its derivative may be copolymerized with the diaminobenzene derivative represented by the general formula (1) (hereinafter referred to simply as the diamine(1)) and other common diamines (hereinafter referred to simply as common diamines).

The common diamines to be used here are primary diamines commonly used for the synthesis of polyimides, and they are not particularly limited. Specific examples thereof include aromatic diamines such as p-phenylenediamine, m-phenylenediamine, 2,5-diaminotoluene, 2,6-diaminotoluene, 4,4'-diaminobiphenyl, 3,3'-dimethyl-4,4'-diaminobiphenyl, 3,3'-dimetoxy-4,4,-diaminobiphenyl, diaminodiphenylmethane, diaminodiphenyl ether, 2,2'-diaminodiphenylpropane, bis(3,5-diethyl-4-aminophenyl) methane, diaminodiphenylsulfone, diaminobenzophenone, diaminonaphthalene, 1,4-bis(4-aminophenoxy)benzene, 1,4-bis(4-aminophenyl)benzene, 9,10-bis(4-aminophenyl) anthracene, 1,3-bis(4-aminophenoxy)benzene, 4,4'-bis(4-aminophenoxy)diphenylsulfone, 2,2-bis[4-(4-aminophenoxy)phenyl]propane, 2,2-bis(4-aminophenyl) hexafluropropane and 2,2-bis[4-(4-aminophenoxy)phenyl] hexafluropropane; aliphatic diamines such as bis(4-aminocyclohexyl)methane and bis(4-amino-3-methylcyclohexyl)methane, and aliphatic diamines such as tetramethylenediamine and hexamethylenediamine; as well as diaminocycloxanes such as

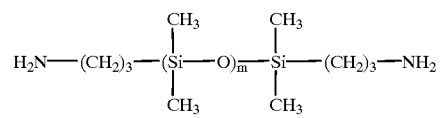

(wherein m is an integer of from 1 to 10). Further, these diamines may be used alone or in combination as a mixture of two or more of them.

By adjusting the proportion of the molar amount of the diamine (1) in the total molar amount of diamines used at the time of polymerization of the polyimide of the present invention, the surface property of the polyimide such as water repellency can be modified, and further in a case where it is used as a liquid crystal alignment film, wettability with liquid crystal, and further, the tilt angle of liquid crystal, can be increased. The proportion of the molar amount of the diamine (1) in the total molar amount of diamines to be used here, is at least 1 mol %.

Further, when it is used as a liquid crystal alignment film, it is common to adjust the proportion of the molar amount of the diamine (1) in the total molar amount of diamines to be used, to be within a range of from 1 mol % to 49 mol % from such a viewpoint that a polyimide having a practically suitable degree of polymerization can easily be obtained, or that the tilt angle required in a common liquid crystal display system (such as a super twisted nematic system) is usually at a level of from a few degrees to about 10 degrees in many cases.

The tetracarboxylic acid and its derivative, and the above mentioned diamine, are reacted and polymerized to obtain a polyimide precursor, and then this is converted to an imide by ring closure. As the tetracarboxylic acid and its derivative to be used here, it is common to employ tetracarboxylic dianhydride. The ratio of the molar amount of the tetracarboxylic dianhydride to the total molar amount of the diamine (1) and common diamines, is preferably from 0.8 to 1.2. Like in a usual polycondensation reaction, the polymerization degree of the resulting polymer tends to be large, as the molar ratio becomes close to 1.

If the polymerization degree is too small, the strength of the polyimide film tends to be inadequate. On the other hand, if the polymerization degree is too large, the operation efficiency at the time of formation of the polyimide film tends to be poor in some cases. Accordingly, the polymerization degree of the product in this reaction is preferably from 0.05 to 5.0 dl/g (in N-methylpirrolidone at a temperature of 30° C., concentration: 0.5 g/dl) as calculated as the reduced viscosity of the polyimide precursor solution.

A method for reacting and polymerizing the carboxylic dianhydride and the above diamine, is not particularly limited. It is common to employ a method wherein the above diamine is dissolved in an organic polar solvent such as N-methylpyrrolidone, N,N-dimethylacetamide or N,N-dimethylformamide, and to the solution, the tetracarboxylic dianhydride is added and reacted to synthesize a polyimide precursor, followed by dehydration ring closure for conversion to an imide.

The reaction temperature at the time of the reacting the tetracarboxylic dianhydride and the above mentioned diamine to obtain a polyimide precursor, may be an optional temperature selected within a range of from −20 to 150° C., preferably from −5 to 100° C. Further, this polyimide precursor is subjected to dehydration under heating at a temperature of from 100 to 400° C., or subjected to chemical imide-conversion by means of an imide-conversion catalyst such as pyridine/acetic anhydride, which is commonly used, to obtain a polyimide.

When the polyimide of the present invention is to be used as an insulating film or a protecting film for an electric or electronic element, or as an alignment film for a liquid crystal display device, it is necessary to form a polyimide coating film having a uniform film thickness on a substrate. To form this polyimide coating film, it is usually possible to form a polyimide coating film by coating the polyimide precursor solution by itself on a substrate and heating it for imide-conversion on the substrate. The polyimide precursor solution to be used here may be the above polymer solution by itself, or the formed polyimide precursor may be put into a large excess amount of a poor solvent such as water or methanol to precipitate and recover it, and then it may be used as re-dissolved in a solvent. The solvent for diluting the above polyimide precursor solution and/or the solvent for re-dissolving the precipitated and recovered polyimide precursor, is not particularly limited so long as it is capable of dissolving the polyimide precursor.

Specific examples of such solvents include N-methylpyrrolidone, N,N-dimethylacetoamide, and N,N-dimethylformamide. These solvents may be used alone or as mixed. Further, even in the case of a solvent which is incapable of presenting a uniform solution by itself, such a solvent may be added and used within a range where a uniform solution can be obtained. As such an example, ethyl cellosolve, butyl cellosolve, ethyl carbitol, butyl carbitol, ethyl carbitol acetate or ethylene glycol may be mentioned. Further, for the purpose of improving the adhesion of the polyimide film to the substrate, it is of course preferred to add an additive such as a coupling agent to the obtained polyimide precursor solution. Further, an optional temperature within a range of from 100 to 400° C. may be employed as the temperature for heating for imide-conversion on the substrate. However, particularly preferred is within a range of from 150 to 350° C.

On the other hand, in a case where the polyimide of the present invention is soluble in a solvent, the polyimide precursor obtained by the reaction of the tetracarboxylic dianhydride and the above mentioned diamine, may be imide-converted in the solvent to obtain a polyimide solution. To convert the polyimide precursor to a polyimide in the solution, it is common to employ a method wherein dehydration ring-closure is carried out by heating. This ring closure temperature by dehydration under heating may be an optional temperature selected within a range of from 150 to 350° C., preferably from 120 to 250° C. As another method for converting the polyimide precursor to the polyimide, it is possible to carry out ring closure chemically by means of a known dehydration ring-closing catalyst.

The polyimide solution thus obtained, may be used by itself, or may be precipitated and isolated in a poor solvent such as methanol or ethanol, and then it may be used as re-dissolved in a proper solvent. The solvent for re-dissolution is not particularly limited so long as it is capable of dissolving the polyimide, but as an example, 2-pyrorridone, N-methyl pyrrolidone, N-ethyl pyrrolidone, N-vinyl pyrrolidone, N, N-dimethyl acetoamide, N,N-dimethylformamide or γ-butyrolactone may be mentioned.

Further, even a solvent which is incapable of dissolving this polyimide by itself, may be added to the above solvent within a range not to impair the solubility. As such an example, ethyl cellosolve, butyl cellosolve, ethyl carbitol, butyl carbitol, ethyl carbitol acetate or ethylene glycol may be mentioned. Further, for the purpose of further improving the adhesion of the polyimide film to the substrate, it is of course preferred to add an additive such as a coupling agent to the obtained polyimide solution. This solution is coated on a substrate, and the solvent is evaporated, whereby a polyimide coating film can be formed on the substrate. The temperature at that time may be sufficient so long as the solvent can be evaporated, and usually a temperature of from 80 to 150° C. is sufficient.

Further, when it is used as a liquid crystal alignment film, a polyimide film having a film thickness of from 100 to 3000 Å, is formed on a transparent substrate of e.g. glass or plastic film provided with transparent electrodes, and then, the polyimide film is subjected to rubbing treatment to obtain a liquid crystal alignment film.

Now, the present invention will be described in further detail with reference to Examples, but the present invention is by no means restricted to such examples.

EXAMPLE 1

(Synthesis of 4-(4-trans-n-heptylcyclohexylphenoxy)-1,3-diaminobenzene)

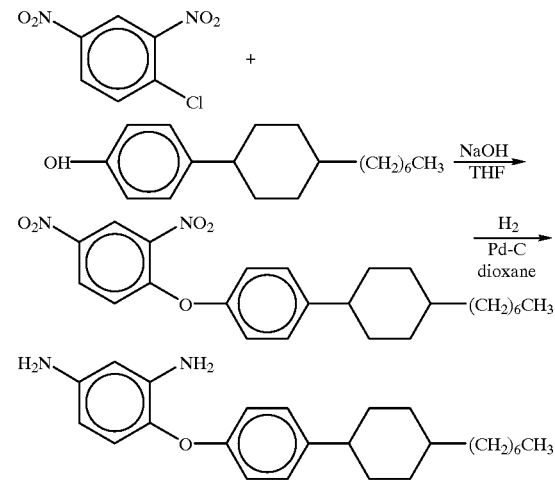

23.3 g of 2,4-dinitrochlorobenzene and 30 g of 4-trans-n-heptylcyclohexylphenol were dissolved in 270 cc of tetrahydrofuran. To this solution, 2.9 g or 18-crown-6-ether and 5.3 g of sodium hydroxide were added, followed by stirring at 50° C. for 5 hours. The reaction mixture was poured into water and, after drying, recrystallized from an acetonitrile aqueous solution to obtain 46.4 g (96%) of 4-(4-trans-n-heptylcyclohexylphenoxy)-1,3-dinitrobenzene. Melting point: 118° C.

40 g of the obtained dinitro compound was dissolved in 500 cc of dioxane. To this solution, 3.8 g of Pd-C was added in a nitrogen atmosphere, followed by stirring overnight in a hydrogen atmosphere. After filtering off Pd-C, the filtrate was poured into water, and precipitated crystals were subjected to filtration and after drying, recrystallized from a solvent mixture of hexane-benzene to obtain 29 g (84%) of 4-trans-n-heptylcyclohexylphenoxy)-1,3-diaminobenzene. Melting point: 128° C.

From the IR, NMR and MASS spectra, the crystals were confirmed to be the desired 4-(4-trans-n-heptylcyclohexylphenoxy)-1,3-diaminobenzene. The analytical results are shown below.

MASS spectrum(m/e): 380(M+)

$^1$H-NMR(CDCL$_3$, δ ppm)7.1(2H,d), 6.8(2H,d), 6.7(1H, d), 6.2(1H,s), 6.1(1H,d), 3.6(4H,bs), 2.5–0.8 (m)

IR(KBr, cm$^{-1}$)3462, 3357, 3222(NH$_2$), 2948, 2917, 2847 (CH$_2$).

EXAMPLE 2
(Synthesis of 4-trans-n-pentylcyclophenoxy)-1,3-diaminobenzene)

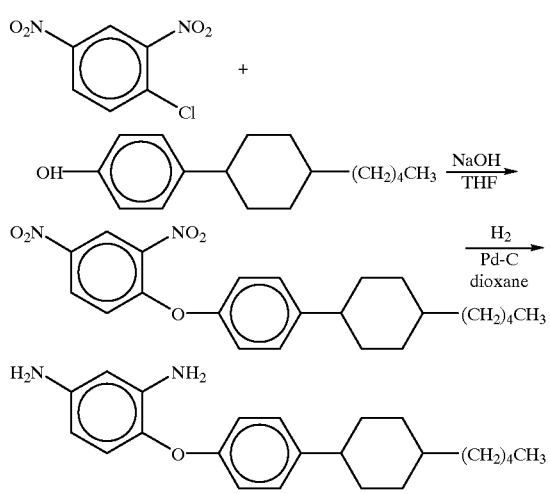

25.95 g of 2,4-dinitrochlorobenzene and 30 g of 4-trans-n-pentylcyclohexylphenol were dissolved in 270 cc of tetrahydrofuran. To this solution, 3.1 g of 18-crown-6-ether and 5.85 g of sodium hydroxide were added, followed by stirring at 50° C. for 5 hours. The reaction mixture was poured into water and after drying, recrystallized from an acetonitrile aqueous solution to obtain 41.9 g (80%) of 4-[4-trans-n-pentylcyclohexylphenoxy]-1,3-dinitrobenzene. Melting point: 118° C.

41.9 g of the obtained dinitro compound was dissolved in 500 cc of dioxane. To this solution, 3.6 g of Pd-C was added under a nitrogen atmosphere, followed by stirring over night in a hydrogen atmosphere. After filtering off Pd-C, the filtrate was poured into water. Precipitated crystals were subjected to filtration and after drying, recrystallized from a solvent mixture of hexane-benzene to obtain 34.4 g (96%) of 4-(4-trans-n-pentylcyclohexylphenoxy)-1,3-diaminobenzene. Melting point: 130° C.

From the IR, NMR and MASS spectra, the crystals were confirmed to be the desired 4-(4-trans-n-pentylcyclohexylphenoxy)-1,3-diaminobenzene. The analytical results are shown below.

MASS spectrum(m/e): 352(M+)

$^1$H-NMR(CDCL$_3$, δ ppm)7.1(2H,d), 6.8(2H,d), 6.7(1H, d), 6.2(1H,s), 6.1(1H,d), 3.6(4H,bs), 2.5–0.8 (m)

IR(KBr, cm$^{-1}$): 3459, 3360, 3213(NH$_2$), 2952, 2917, 2847(CH$_2$)

EXAMPLE 3
(4-trans-n-pentylbicyclohe,xyl-3,5-diaminobenzoate)

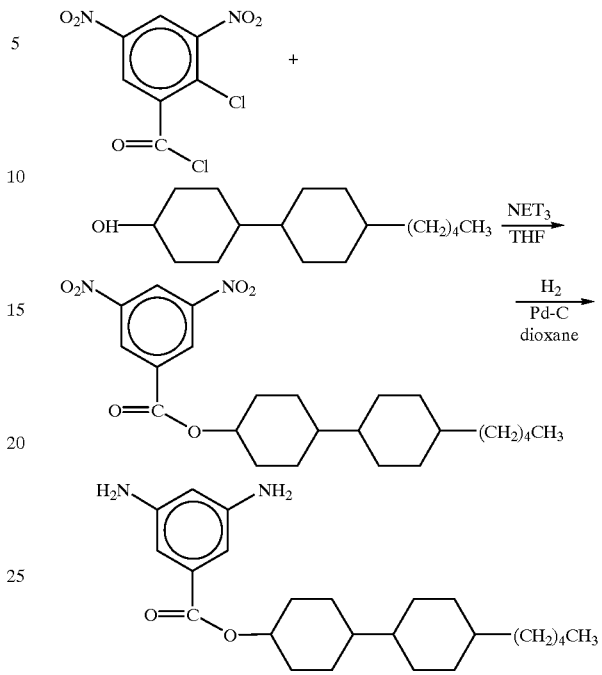

32 g of 4-trans-n-pentylcyclohexylcyclohexanol was dissolved in 600 cc of tetrahydrofuran and 18 g of triethylamine.

To this solution, 29 g of 3,5-dinitrobenzoyl chloride was added, followed by stirring at 50° C. for 1 hour. The reaction mixture was poured into water and after drying, recrystallized from acetonitrile to obtain 45 g (80%) of 4-trans-n-pentylbicyclohexyl-3,5-dinitrobenzoate. Melting point: 146° C.

38 g of the obtained dinitro compound was dissolved in 650 cc of dioxane. To this solution, 3.1 g of Pd-C was added under a nitrogen atmosphere, followed by stirring overnight in a hydrogen atmosphere. After filtering off Pd-C, the filtrate was poured into water. The precipitated crystals were subjected to filtration and after drying, recrystallized from a solvent mixture of hexane-benzene to obtain 31 g (71%) of the obtained product. Melting point: 175° C.

MASS spectrum(m/e): 386(M+)

$^1$H-NMR(CDCL$_3$, δ ppm) 6.8(2H,s), 6.2(1H,s), 4.9(1H, bs), 3.7(3H,bs), 2.1–0.8(m)

IR(KBr, cm$^{-1}$): 3416, 3395, 3304, 3206(NH$_2$), 2938, 2917, 2847(CH$_2$).

EXAMPLE 4
(Synthesis of 4-(4-trans-n-propylcyclohexylphenoxy)-1,3-diaminobenzene)

Using 23.3 g of 2,4-dinitrochlorobenzene and 23.9 g of 4-trans-n-propylcyclohexylphenol, in the same manner as in Example 1, 35.7 g (81%) of 4-(4-trans-n-propylcyclohexylphenoxy)-1,3-dinitrobenzene was obtained. Melting point: 134° C.

Using 11.2 g of the obtained dinitro compound, reduction and recrystallization were carried out in the same manner as in Example 1 to obtain 7.4 g (78%) of 4-(4-trans-n-propylcyclohexylphenoxy)-1,3-diaminobenzene. Melting point: 131° C.

From the IR, NMR and MASS spectra, the crystals were confirmed to be the desired 4-( 4-trans-n- butylcyclohexylphenoxy)-1,3-diaminobenzene. The analytical results are shown below.

MASS spectrum(m/e): 324(M+)

$^1$H-NMR(CDCL$_3$, δ ppm): 7.1(2H,d), 6.8(2H,d), 6.7(1H, d), 6.2(1H,s), 6.1(1H,d), 3.6(4H,bs),2.1–0.8(m)

IR(KBr, cm$^{-1}$):3416, 3395, 3332, 3227(NH$_2$), 2932, 2924, 2847(CH$_2$).

EXAMPLE 5

(Synthesis of 4-(4-trans-butylcyclohexylphenoxy)-1,3-diaminobenzene)

Using 23.3 g of 2,4-dinitrochlorobenzene and 25.5 g of 4-trans-n-butylcyclohexylphenol, in the same manner as in Example 1, 37.3 g (81%) of 4-(4-trans-n-butylcyclohexylphenoxy)-1,3-dinitrobenzene was obtained. Melting point: 122° C.

Using 21.9 g of the obtained dinitro compound, reduction and recrystallization were carried out in the same manner as in Example 1 to obtain 16.8 g (90%) of 4-(4-trans-n-butylcyclohexylphenoxy)-1,3-diaminobenzene. Melting point:129° C.

From the IR, NMR and MASS spectra, the crystals were confirmed to be the desired 4-(4-trans-n-propylcyclohexyl-1,3-diaminobenzene. The analytical results are shown below.

MASS spectrum(m/e): 338(M+)

$^1$H-NMR(CDCL$_3$, δ ppm): 7.1(2H,d), 6.8(2H,d), 6.7(1H, d), 6.2(1H,s), 6.1(1H,d), 3.6(4H,bs), 2.5–0.8(m)

IR(KBr, cm$^{-1}$):3459, 3360, 3332, 3213(NH$_2$), 2959, 2917, 2847(CH$_2$).

EXAMPLE 6

(Synthesis of 4-trans-n-propylbicyclohexyl-3,5-diaminobenzoate)

Using 23.6 g of 4-trans-n-propylcyclohexylcyclohexanol and 24.2 g of 3,5-dinitrobenzoyl chloride, in the same manner as in Example 3, 19.3 g (44%) of 4-trans-n-propylbicyclohexyl-3,5-dinitrobenzoate was obtained. Melting point: 134° C.

Using 19.3 g of the obtained dinitro compound, reduction and recrystallization were carried out in the same manner as in Example 3, to obtain 10 g (61%) of 4-trans-n-propylbicyclohexyl-3,5-diaminobenzoate. Melting point: 157° C.

From the IR, NMR and MASS spectra, the crystals were confirmed to be the desired 4-(4-trans-n-propylbicyclohexyl)-3,5-diaminobenzoate. The analytical results are shown below.

MASS spectrum(m/e): 359(M+)

$^1$H-NMR(CDCL$_3$, δ ppm): 6.8(2H,S), 6.2 (1H,s), 4.9(1H, bs), 3.7(3H,bs), 2.1–0.8(m)

IR(KBr, cm$^{-1}$):3416, 3395, 3304, 3213(NH$_2$), 2945, 2917, 2354(CH$_2$).

EXAMPLE 7

(Synthesis of 4-trans-n-butylbicyclohexyl-3,5-diaminobenzoate)

Using 23 g of 4-trans-n-butylcyclohexylcyclohexanol and 22.3 g of 3,5-dinitrobenzoyl chloride, in the same manner as in Example 3, 14.7 g (67%) of 4-trans-n-butylbicyclohexyl-3,5-dinitrobenzoate was obtained. Melting point: 124° C.

Using 14.7 g of the obtained dinitro compound, reduction and recrystallization were carried out in the same manner as in Example 3 to obtain 10 g (79%) of 4-trans-n-butylbicyclohexyl-3,5-diaminobenzoate. Melting point: 110° C.

From the IR, NMR and MASS spectra, the crystals were confirmed to be the desired 4-trans-n-butylbicyclohexyl-3, 5-diaminobenzoate. The analytical results are shown below.

MASS spectrum(m/e): 373(M+)

$^1$H-NMR(CDCL$_3$, δ ppm): 6.8(2H,s), 6.2(1H,s), 4.9(1H, bs), 3.7(3H,bs), 2.1–0.8(m)

IR(KBr, cm$^{-1}$): 3452, 3360, 3191(NH$_2$), 2924, 2854 (CH$_2$)

EXAMPLE 8

(Production of a Polyimide)

5 g (13.1 mmol) of 4-(4-trans-n-heptylcyclohexylphenoxy)-1,3-diaminobenzene obtained in Example 1 and 2.58 g (13.1 mmol) of 1,2,3,4-cyclobutanoic dianhydride were dissolved in 43 g of N-methylpyrrolidone, followed by stirring at 20° C. for 4 hours for a polycondensation reaction to obtain a polyimide precursor solution.

The reduced viscosity of the obtained polyimide precursor was 0.51 dl/g (concentration: 0.5 g/dl in NMP at 30° C.).

This solution was coated on a glass substrate and heat-treated at 250° C. for 1 hour to obtain a uniform polyimide coating film.

The obtained coating film was subjected to IR measurement and confirmed to be a polyimide containing a heptylcyclohexylphenyloxy group.

EXAMPLES 9 to 14

(Syntheses of Polyimides)

Using the diamines obtained in Examples 2 to 7, polyimide precursor solutions were prepared in the same manner as in Example 8. The reduced viscosities of the obtained polyimide precursor solutions (concentration: 0.5 g/dl, in NMP at 30° C.) were 0.50 dl/g in Example 9, 0.52 dl/g in Example 10, 0.47 dl/g in Example 11, 0.51 dl/g in Example 12, 0.49 dl/g in Example 13 and 0.50 dl/g in Example 14. Further, IR measurements were carried out in the same manner as in Example 4, whereby they were confirmed to be polyimides having alkyl cyclic substituents corresponding to the respective diamines.

EXAMPLES 15 to 21

(Production of Liquid Crystal Alignment Films)

Then, the polyimide precursor solutions obtained in Examples 8 to 14 were coated on glass substrates and heat-treated at a predetermined temperature to form polyimide coating films. In accordance with the following methods, the water repellency of the polyimide surface, and the alignment property and the tilt angle of liquid crystal when it is used as a liquid crystal alignment film, were measured. The results are shown in a Table.

Evaluation of water repellency: A polyimide precursor solution was diluted with N-methylpyrrolidone to obtain a solution having a resin concentration of 6%, which was spin-coated at 3500 rpm on a glass substrate and heat-treated at 80° C. for 5 minutes and 250° C. for 1 hour to form a uniform polyimide coating film, whereupon the contact angles of water and diiodomethane on this coating film are measured, and the surface energy of the polyimide was calculated by the Fowkes formula.

Evaluation of tilt angle: A polyimide precursor solution was diluted with N-methylpyrrolidone to obtain a solution having a resin concentration of 6%, which was spin-coated at 3500 rpm on a glass substrate provided with transparent electrodes and heat-treated at 80° C. for 10 minutes and at 250° C. for 1 hour to form a uniform polyimide coating film. This coating film was rubbed with a cloth. Then, a pair of such substrates were assembled with a spacer of 25 μm interposed therebetween so that the rubbing directions would be in parallel to each other, and liquid crystal (ZLI-2293, manufactured by Merck Co.) was injected to obtain a cell with homogeneous alignment.

With respect to this cell, uniformity of the liquid crystal alignment was confirmed under a polarization microscope, and with respect to one immediately after injection of liquid crystal and one heat-treated at 120° C. for 1 hour, the tilt angles were measured by a magnet capacitive null method. The results are shown in Table 1. Further, for the purpose of comparison, the following diamines were synthesized, and polyimide precursors were prepared by using them, and liquid crystal alignment films were prepared and evaluated in the same manner. The results are also shown in Table 1.

COMPARATIVE EXAMPLE 1

In the same manner as in Example 1, 4-(4-cyclohexylphenoxy)-1,3-diaminobenzene (melting point 101° C.) was obtained. Using the obtained diamine, in the same manner as in Example 8, a polyimide precursor solution was prepared from 1,2,3,4-cyclobutane tetracarboxylic dianhydride. Then, in accordance with Example 15, preparation of an alignment film and evaluation of the water repellency and the tilt angle, were carried out. The results are shown in Table 1.

COMPARATIVE EXAMPLE 2

Using 4-bicyclohexyl-3,5-diaminobenzoate (yellow oil) i.e. a diamine synthesized in the same manner as in Example 3, in the same manner as in Example 4, a polyimide precursor solution was prepared from 1,2,3,4-cyclobutane tetracarboxylic dianhydride. Then, in accordance with Examples 7 to 9, preparation of an alignment film and evaluation of the water repellency and tilt angle were carried out.

EVACUATION RESULTS

TABLE 1

| Example | Polyimide (Example) | Diamine (Example) | Surface energy (dyn/cm) | Tilt angle (°) |
| --- | --- | --- | --- | --- |
| 15 | 8 | 1 | 33.0 | 89 (90) |
| 16 | 9 | 2 | 34.0 | 89 (90) |
| 17 | 10 | 3 | 35.0 | 89 (89) |
| 18 | 11 | 4 | 36.9 | 88.1 (87.4) |
| 19 | 12 | 5 | 36.1 | 90.0 (90.0) |
| 20 | 13 | 6 | 37.5 | 90.0 (81.2) |
| 21 | 14 | 7 | 37.0 | 81.6 (85.0) |
| Comparative Example | 1 | 1 | 42.8 | 2.4 (1.3) |
| | 2 | 2 | 41.2 | 32.8 (15.9) |

The number in the brackets ( ) of the tilt angle is the value after heat treatment at 120° C. for 1 hour.

With each cell, uniform alignment free from any defect was observed, and a high tilt angle was obtained.

EXAMPLE 22

6.92 g of 4-(4-trans-n-heptylcyclohexylphenoxy)-1,3-diaminobenzene of Example 1 and 8.09 g of 2,2-bis(4-aminophenoxyphenyl)propane, as diamines, and 7.59 g of 1,2,3,4,-cyclobutane tetracarboxylic dianhydride as a tetracarboxylic dianhydride, were dissolved in 78 g of N-methylpyrrolidone in a 200 mml flask in a nitrogen stream, followed by stirring at 20° C. for 4 hours for a polycondensation reaction to obtain a polyimide precursor solution. The reduced viscosity of the obtained polyimide precursor was 0.45 (concentration: 0.5 g/dl, in NMP at 30° C.).

Further, this solution was coated on a glass substrate and heat-treated at 180° C. or 250° C. for 1 hour to form a polyimide coating film. The obtained coating film was subjected to IR measurements and confirmed to be a polyimide having a heptylcyclohexylphenoxy group.

Using the obtained polyimide precursor, the water repellency of the polyimide coating film was examined, whereby its surface energy was 36 dyn/cm with one heat-treated at 180° C. for 1 hour and 37 dyn/cm with one heat-treated at 250° C. for 1 hour.

Further, a liquid crystal cell was prepared, and the alignment property was examined, whereby uniform alignment free from any defect, was obtained.

Further, using this cell, the tilt angle was measured, and it was 43° immediately after injection of liquid crystal with one heat-treated at 180° C. for 1 hour, and 50° with one heat-treated at 120° C. for 1 hour. Further, it was 35° immediately after injection of liquid crystal with one heat-treated at 250° C. for 1 hour, and 35° with one heat-treated at 120° C. for 1 hour.

EXAMPLE 23

3.48 g of 4-(4-trans-n-heptylcyclohexylphenoxy)-1,3-diaminobenzene and 12,2 g of 2,2-bis(4-aminophenoxyphenyl)propane, as diamines, and 7.64 g of 1,2,3,4-cyclobutane tetracarboxylic dianhydride as a tetracarboxylic dianhydride, were dissolved in 82 g of N-methylpyrrolidone in a 200 ml flask in a nitrogen stream, followed by stirring at 20° C. for 4 hours to carry out a polycondensation reaction to obtain a polyimide precursor solution.

The reduced viscosity of the obtained polyimide precursor was 0.47 (concentration: 0.5 g/dl, in NMP at 30° C.).

Further, this solution was coated on a glass substrate and heat-treated at 180° C. or 250° C. for 1 hour to form a polyimide coating film. The obtained coating film was subjected to IR measurements and confirmed to be a polyimide having a heptylcyclohexylphenoxy group. Using the obtained polyimide precursor, the water repellency of the polyimide coating film was examined, whereby the surface energy was 40 dyn/cm with one heat-treated at 180° C. for 1 hour and 41 dyn/cm with one heat-treated at 250° C. for 1 hour.

Further, a liquid crystal cell was prepared, and the alignment property was examined, whereby uniform alignment without any defect was obtained.

Further, using this cell, the tilt angle was measured, and it was 6° immediately after injection of liquid crystal with one heat-treated at 180° C. for 1 hour, and 6° with one heat-treated at 120° C. for 1 hour. Further, with one heat-treated at 250° C. for 1 hour, it was 6° immediately after injection of liquid crystal, and 7° with one heat-treated at 120° C. for 1 hour.

EXAMPLE 24

9.50 g of 4-(4-trans-n-pentylcyclohexylphenoxy)-1,3-diaminobenzene of Example 2 and 11.06 g of 2,2-bis(4-aminophenoxyphenyl)propane, as diamines, and 10.36 g of 1,2,3,4-cyclobutane tetracarboxylic dianhydride as a tetracarboxylic dianhydride, were dissolved in 195 g of N-methylpyrrolidone in a 200 ml in a nitrogen stream, followed by stirring at 20° C. for 4 hours for a polycondensation reaction to obtain a polyimide precursor solution.

The reduced viscosity of the obtained polyimide precursor was 0.40 (concentration 0.5 g/dl, in NMP at 30° C.).

Further, this solution was coated on a glass substrate and heat-treated at a 180° C. or 250° C. for 1 hour to form a polyimide coating film. The obtained coating film was subjected to IR measurements and confirmed to be a polyimide having a pentylcyclohexylphenoxy group.

Using the obtained polyimide precursor, the water repellency of the polyimide coating film was examined, whereby its surface energy was 37 dyn/cm with one heat-treated at 180° C. for 1 hour and 37 cyn/cm with one heat-treated at 250° C. for 1 hour.

Further, a liquid crystal cell was prepared and the alignment property was examined, whereby uniform alignment without any defect, was obtained. Further, using this cell, the tilt angle was measured, and it was 36° immediately after injection of liquid crystal with one heat-treated at 180° C. for 1 hour, and 37° with one subsequently heat-treated at 120° C. for 1 hour. Further, it was 20 immediately after injection of liquid crystal with one heat-treated at 250° C. for 1 hour, and 21° with one heat-treated subsequently at 120° C. for 1 hour.

EXAMPLE 25

4.80 g of 4-(4-trans-n-pentylcyclohexylphenoxy)-1,3-diaminobenzene of Example 2 and 16.77 g of 2,2-bis(4-aminophenoxyphenyl)propane, as diamines, and 10.47 g of 1,2,3,4-cyclobutane tetracarboxylic dianhydride as a tetracarboxylic dianhydride, were dissolved in 180 g of N-methylpyrrolidone in a 200 ml flask in a nitrogen stream, followed by stirring at 20° C. for 4 hours to carry out a polycondensation reaction to obtain a polyimide precursor solution.

The reduced viscosity of the obtained polyimide precursor was 0.41 (concentration:0.5 g/dl, in NMP at 30° C.).

Further, this solution was coated on a glass substrate and heat-treated at 180° C. or 250° C. for 1 hour to form a polyimide coating film. The obtained coating film was subjected to IR measurements and confirmed to be a polyimide having a pentylcyclohexylphenoxy group.

Using the obtained polyimide precursor, the water repellency of the polyimide coating film was examined, whereby its surface energy was 41 dyn/cm with one heat-treated at 180° C. for 1 hour, and 43 dyn/cm with one heat-treated at 250° C. for 1 hour.

Further, a liquid crystal cell was prepared, and the alignment property was examined, whereby uniform alignment free from any defect, was obtained.

Further, using this cell, the tilt angle was measured, and it was 5° immediately after injection of liquid crystal with one heat-treated at 180° C. for 1 hour and 5° with one heat-treated subsequently at 120° C. for 1 hour. Further, it was 7° immediately after injection of liquid crystal with one heat-treated at 250° C. for 1 hour, and 7° with one heat-treated subsequently at 120° C. for 1 hour.

EXAMPLE 26

6.00 g of pentylbicyclohexyl 3,5-diaminobenzoate of Example 3 and 6.37 g of 2,2-bis(4-aminophenoxyphenyl)propane, as diamines, and 5.97 g of 1,2,3,4-cyclobutane tetracarboxylic acid as a tetracarboxylic acid, were dissolved in 103 g of N-methylpyrrolidone in a 200 ml flask in a nitrogen stream, followed by stirring at 20° C. for 4 hours for a polycondensation reaction to obtain a polyimide precursor solution.

The reduced viscosity of the obtained polyimide precursor was 0.46(concentration: 0.5 g/dl, in NMP at 30° C.).

Further, this solution was coated on a glass substrate and heat-treated at 180° C. or 250° C. for 1 hour to form a polyimide coating film. The obtained coating film was subjected to IR measurements and confirmed to be a polyimide having a pentylbicyclohexyloxycarbonyl group.

Using the obtained polyimide precursor, the water repellency of the polyimide coating film was examined, whereby its surface energy was 37 dyn/cm with one heat-treated at 180° C. for 1 hour and 40 dyn/cm with one heat-treated at 250° C. for 1 hour.

Further, a liquid crystal cell was prepared, and the alignment property was examined, whereby uniform alignment without any defect was obtained.

Further, using this cell, the tilt angle was measured, and it was 80° immediately after injection of liquid crystal with one heat-treated at 180° C. for 1 hour, and 85 with one heat-treated subsequently at 120° C. for 1 hour. Further, it was 59° immediately after injection of liquid crystal with one heat-treated at 250° C. for 1 hour, and 62° with one heat-treated subsequently at 120° C. for 1 hour.

EXAMPLE 27

3.00 g of pentylbicyclohexyl 3,5-diaminobenzoate of Example 3 and 9.56 g of 2,2,-bis(4-aminophenoxyphenyl)propane, as diamines, and 5.97 g of 1,2,3,4-cyclobutane tetracarboxylic dianhydride as a tetracarboxylic dianhydride, were dissolved in 100 g of N-methylpyrrolidone in a 200 ml flask in a nitrogen stream, followed by stirring at 20° C. for 4 hours for a polycondensation reaction to obtain a polyimide precursor solution.

The reduced viscosity of the obtained polyimide precursor was 0.49 (concentration: 0.5 g/dl, in NMP at 30° C.)

Further, this solution was coated on a glass substrate and heat-treated at 180° C. or 250° C. for 1 hour to form a polyimide coating film. The obtained coating film was subjected to IR measurement and confirmed to be a polyimide having a pentylbicyclohexyloxycarbonyl group.

Using the obtained polyimide precursor, the water repellency of the polyimide coating film was examined, whereby its surface energy was 40 dyn/cm with one heat-treated at 180cC for 1 hour and 43 dyn/cm with one heat-treated at 250° C. for 1 hour.

Further, a liquid crystal cell was prepared, and the alignment property was examined, whereby uniform alignment without any defect, was obtained.

Further, using this cell, the tilt angle was measured, and it was 24° immediately after injection of liquid crystal with one treated at 180° C. for 1 hour, and 30° with one heat-treated subsequently at 120° C. for 1 hour. Further, it was 25° immediately after injection of liquid crystal with one heat-treated at 250° C. for 1 hour, and 31° with one heat-treated subsequently at 120° C. for 1 hour.

COMPARATIVE EXAMPLE 3

1.60 g of hexadecyloxy-2,5-diaminobenzene as a diamine and 1.80 g of 1,2,3,4-cyclobutane tetracarboxylic dianhydride as a tetracarboxylic dianhydride, were dissolved in 31 g of N-methylpyrrolidone in a 100 ml flask in a nitrogen stream, followed by stirring at 20° C. for 4 hours for a polycondensation reaction to obtain a polyimide precursor solution.

The reduced viscosity of the obtained polyimide precursor was 0.49 (concentration: 0.5 g/dl, in NMP at 30° C.).

Further, this solution was coated on a glass substrate and heat-treated at 180° C. or 250° C. for 1 hour to form a polyimide coating film. The obtained coating film was subjected to IR measurements and confirmed to be a polyimide having a hexadecyloxy group.

Using the obtained polyimide precursor, the water repellency of the polyimide coating film was examined, whereby the surface energy was 35 dyn/cm with one heat-treated at 180° C. for 1 hour and 39 dyn/cm with one heat-treated at 250° C. for 1 hour.

Further, a liquid crystal cell was prepared, and the alignment property was examined, whereby uniform alignment without any defect, was obtained.

Further, using this cell, the tilt angle was measured, and it was 77° immediately after injection of liquid crystal with one heat-treated at 180° C. for 1 hour, and 22° with one heat-treated subsequently at 120° C. for 1 hour. Further, it was 11° immediately after injection of liquid crystal with one heat-treated at 250° C. for 1 hour and 9° with one heat-treated subsequently at 120° C. for 1 hour.

The following Table 2 shows the results of measurement of the tilt angles in Examples 22 to 27 and Comparative Example 3, as summarized.

TABLE 2

| Example | 180° C. cure Tilt angle (°) | 250° C. cure Tilt angle (°) |
|---|---|---|
| 22 | 43(50) | 35(35)* |
| 23 | 6(9) | 6(7) |
| 24 | 36(37) | 20(21) |
| 25 | 5(5) | 7(7) |
| 26 | 80(85) | 59(62) |
| 27 | 24(30) | 25(31) |
| Comparative Example | | |
| 3 | 70(33) | 11(9) |

*The number in the brackets ( ) is the value after the heat treatment at 120° C.

INDUSTRIAL APPLICABILITY

The diaminobenzene derivative of the present invention is easy to prepare, and by synthesizing a polyimide by using this as a starting material, it is possible to modify the surface properties of the polyimide, such as thermal resistance and water repellency. Further, in the case of a polyimide for an alignment film for a liquid crystal display device, it is possible to uniformly align liquid crystal to obtain a high tilt angle. Further, in this case, it has characteristics such that it has a high tilt angle, and the tilt angle undergoes no substantial change even by heat treatment.

What is claimed is:

1. A diaminobenzene derivative represented by the general formula (1):

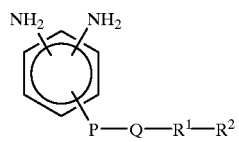

[1]

wherein P is a single bond or a bivalent organic group selected from —O—, —COO— and —CONH—, Q is a cyclic substituent selected from an aromatic ring, an aliphatic ring, a hetero ring and their substitution products, $R^1$ is an aliphatic ring, and $R^2$ is a $C_{1-22}$ straight chain alkyl group.

2. The diaminobenzene derivative according to claim 1, wherein P in the general formula (1) is —O—.

3. The diaminobenzene derivative according to claim 1, wherein Q in the general formula (1) is a benzene ring.

4. The diaminobenzene derivative according to claim 1, wherein $R^1$ in the general formula (1) is a cyclohexane ring.

5. A polyimide obtained by reacting a diamine containing at least 1 mol % of a diaminobenzene derivative represented by the general formula (1):

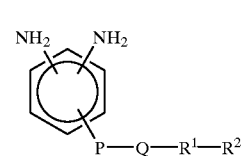

[1]

wherein P is a single bond or a bivalent organic group selected from —O—, —COO— and —CONH—, Q is a cyclic substituent selected from an aromatic ring, an aliphatic ring, a hetero ring and their substitution products, and $R^1$ is an aliphatic ring, and $R^2$ is a $C_{1-22}$ straight chain alkyl group, with a tetracarboxylic acid an its derivative to obtain a polyimide precursor having a reduced viscosity of from 0.05 to 5.0 dl/g in N-methylpyrrolidone at a temperature of 30° C., concentration: 0.5 g/dl and ring-closing it, and having a repeating unit represented by the general formula (2):

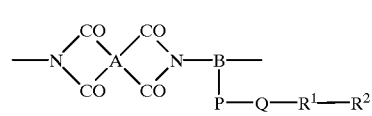

[2]

wherein A is a tetravalent organic group constituting a tetracarboxylic acid, B is a bivalent organic group constituting a diamine, and P, Q, $R^1$ and $R^2$ are the same as in the above formula (1)).

6. The polyimide according to claim 5, wherein P in the general formula (1) is —O—.

7. The polyimide according to claim 5, wherein Q in the general formula (1) is a benzene ring.

8. The polyimide according to claim 5, wherein $R^1$ in the general formula (1) is a cyclohexane ring.

9. The polyimide according to claim 5, wherein the tetracarboxylic acid and its derivative, are an alicyclic tetracarboxylic acid and its derivative.

10. The polyimide according to claim 1, wherein the tetracarboxylic acid and its derivative, are 1,2,3,4-cyclobutane tetracarboxylic dianhydride and its derivative.

11. The polyimide according to claim 1, wherein the tetracarboxylic acid and its derivative, are 3,4-dicarboxy-1,2,3,4-tetrahydro-1-naphthalene succinic dianhydride and its derivative.

12. A liquid crystal alignment film containing a polyimide having a repeating unit represented by the general formula (2):

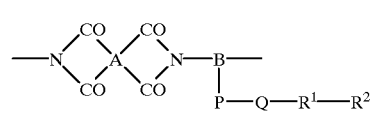

[2]

wherein A is a tetravalent organic group constituting a tetracarboxylic acid, B is a bivalent organic group constituting a diamine, and P, Q, $R^1$ and $R^2$ are the same as in the above formula (1).

13. The liquid crystal alignment film according to claim 12, wherein P in the general formula (2) is —O—.

14. The liquid crystal alignment film according to claim 12, wherein Q in the general formula (2) is a benzene ring.

15. The liquid crystal alignment film according to claim 12, wherein $R^1$ in the general formula (2) is a cyclohexane ring.

16. The liquid crystal alignment film according to claim 12, wherein A in the general formula (2) is a residue of an alicyclic tetracarboxylic acid and its derivative.

17. The liquid crystal alignment film according to claim 16, wherein the alicyclic tetracarboxylic acid and its derivative, are 1,2,3,4-cyclobutene tetracarboxylic dianhydride and its derivative.

18. The liquid crystal alignment film according to claim 16, wherein the alicyclic tetracarboxylic acid and its derivative, are 3,4-dicarboxy-1,2,3,4-tetrahydro-1-naphthalene succinic dianhydride and its derivative.

19. The liquid alignment film according to claim 12, wherein the polyimide is one wherein —P—Q—$R^1$—$R^2$ in the general formula (2) is represented by the general formula (3):

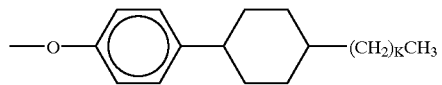

[3]

wherein K is an integer of from 0 to 21.

20. The liquid crystal alignment film according to claim 19, wherein the polyimide is one obtained from diamine components, wherein a diamine component having a side chain of the general Formula (3) constitutes from 1 to 49 mol % of all diamine components.

* * * * *